United States Patent [19]

Nishi et al.

[11] Patent Number: 5,041,579

[45] Date of Patent: Aug. 20, 1991

[54] PLATINUM COMPLEXES AND USES THEREWITH

[75] Inventors: Seiichi Nishi; Kazuo Ohishi; Kunisuke Izawa, all of Kawasaki; Tsuyoshi Shiio, Kamakura; Tetsuo Suami, Musashino, all of Japan

[73] Assignee: Ajinomoto Co., Inc., Tokyo, Japan

[21] Appl. No.: 257,899

[22] Filed: Sep. 23, 1988

[30] Foreign Application Priority Data

Sep. 26, 1987 [JP] Japan .................................. 62-241720
Aug. 26, 1988 [JP] Japan .................................. 63-211695

[51] Int. Cl.$^5$ ...................... C07F 15/00; A61K 31/28; A61K 31/555
[52] U.S. Cl. ........................................ 556/137; 546/5; 548/403
[58] Field of Search ....................... 514/492, 184, 188; 556/137; 546/5; 548/403

[56] References Cited

U.S. PATENT DOCUMENTS 4,670,458  6/1987  Hlavka et al. ........................ 514/492
4,786,725  11/1988  Amundsen et al. ................ 556/137

FOREIGN PATENT DOCUMENTS 61-286396  12/1986  Japan .................................. 556/137

OTHER PUBLICATIONS

CA106; 42856w of Qu et al., *Yingyong Huaxue*, 1986, 3(3), 25–9.

*Primary Examiner*—Paul F. Shaver
*Attorney, Agent, or Firm*—Oblon, Spivak, McClelland, Maier & Neustadt

[57] ABSTRACT

Platinum complexes of cis-diaminocyclohexanol or cis-diaminocyclohexane, with the exclusion of platinum complexes of 2-deoxystreptamine, having high anti-tumor activity, low toxicity, water-solubility and exhibiting no cross-resistance to cis-platin.

6 Claims, No Drawings

PLATINUM COMPLEXES AND USES THEREWITH

BACKGROUND OF THE INVENTION

1. Field of the Invention

The invention relates to water-soluble platinum complexes of cis-diaminocyclohexanol or cis-diaminocyclohexane, and to anti-tumor agents containing the same.

2. Description of the Background

Since the high anti-tumor activity of cisplatin [cis-dichlorodiamineplatinum(II)] was reported in Nature, 222, 385 (1969), extensive studies have been made on this compound as an anti-tumor agent. As a result, it is widely used clinically as an anti-cancer agent of high efficacy throughout the world. However, it has severe side effects, such as toxicity to the kidney, nausea, emesis and bradyacusia, and readily causes drug resistance. Under the circumstances, researchers over the world have attempted to synthesize second-generation platinum complexes which have medical efficacy comparable with cisplatin or but which are free from toxicity to the kidney and other side effects, and show no cross resistance with cisplatin. As a result, the platinum(II) complex of cis-dichloro-1,2-diaminocyclohexane has been found to have some promise [Chem. Biol. Interactions, 5, 415 (1972)], but this substance has low solubility in water. Additionally, platinum complexes have been prepared by using diaminocyclohexanols as the amine component, which complexes show high inhibitory action particularly against the growth of L 1210 (mouse leukemia cells) and S-180. See Japanese Patent Kokai No. 286396 (1986).

However, all of these complexes have poor water solubility, which make them impractical for clinical use.

Thus, a need continues to exist for a platinum-containing anti-tumor agent which is readily soluble in water, exhibits high anti-tumor activity, has low toxicity and exhibits no cross-resistance with cis-platin.

SUMMARY OF THE INVENTION

Accordingly, it is an object of the present invention to provide a platinum-containing anti-tumor agent which has high anti-tumor activity but low toxicity.

It is also an object of this invention to provide such an anti-tumor agent having good water-solubility.

Further, it is an object of the present invention to provide such an anti-tumor agent which exhibits no cross-resistance to cis-platin.

The above objects and other objects which are described hereinbelow are provided by platinum complexes of cis-diaminocyclohexanol or cis-diaminocyclohexane having one or more of the following formulas:

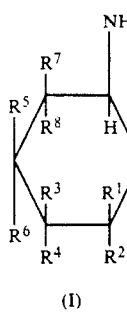

(I)

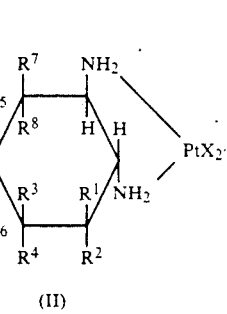

(II)

-continued

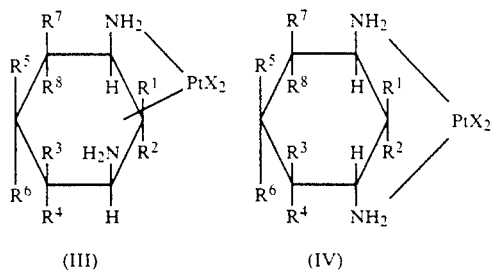

(III)            (IV)

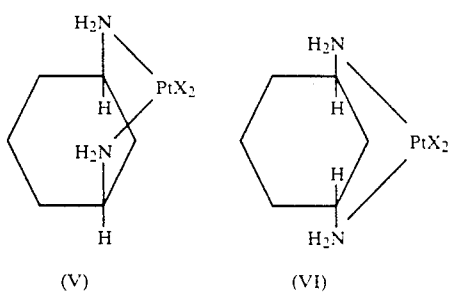

(V)            (VI)

wherein $X_2$ is a radical having one or more of the following structural formulas:

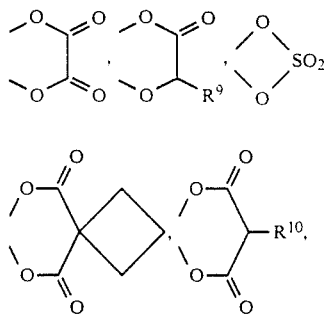

wherein each of $R^1$–$R^8$, which are the same or different, are a hydrogen atom or hydroxyl group, in which at least one of said R groups is a hydroxyl group, and wherein at least one of the two hydrogen atoms on each carbon atom constituting a cyclohexane ring is unsubstituted; $R^9$ is hydrogen, hydroxyl, a lower alkyl, or phenyl; and $R^{10}$ is hydrogen, hydroxyl, an unsubstituted amino group or an amino group which is substituted by a dimethylamino, N-acetylamino, piperidyl and pyrrolidyl group; a lower alkyl, a lower alkoxy, phenyl, or phenoxy, wherein platinum complexes of 2-deoxystreptamine in which $X_2$ is the residue of a dicarboxylic acid derivative are excluded.

DETAILED DESCRIPTION OF THE PREFERRED EMBODIMENTS

In accordance with the present invention are provided platinum complexes of cis-diaminocyclohexanol cis-diaminocyclohexane having one or more of the following formulas:

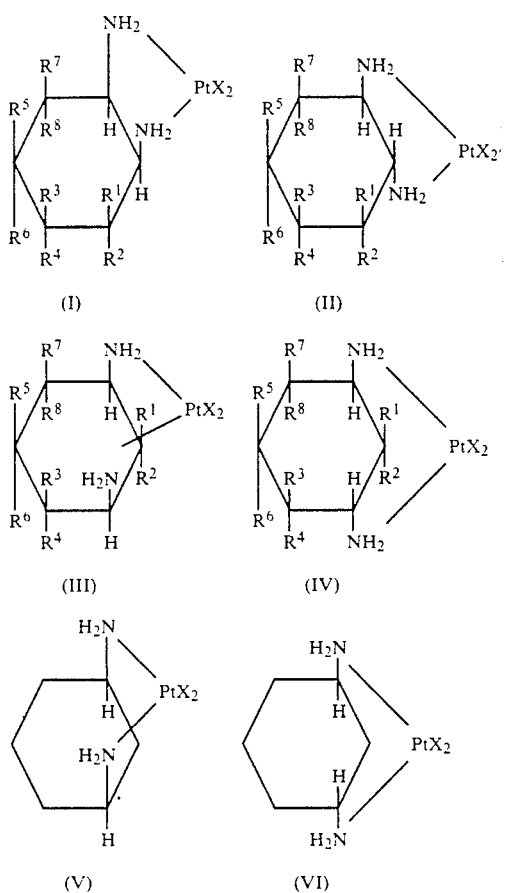

(I)  (II)  (III)  (IV)  (V)  (VI)

In the above formulas, $X_2$ denotes a radical represented by any one of the following structural formulas:

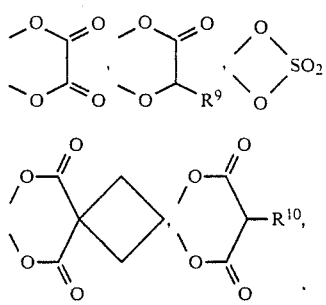

wherein each of $R^1$-$R^8$, which are the same or different, are a hydrogen atom or hydroxyl group, in which at least one of the R groups is a hydroxyl group, and wherein at least one of the two hydrogen atoms on each carbon atom constituting the cyclohexane ring is unsubstituted; $R^9$ stands for hydrogen, hydroxyl, a lower alkyl of 1 to 5 carbon atoms, or phenyl; $R^{10}$ is hydrogen, hydroxyl, an unsubstituted amino group or amino group which is substituted by, for example, a dimethylamino, N-acetylamino, piperidyl and pyrrolidyl group, a lower alkyl of 1 to 5 carbon atoms, a lower alkoxy of 1 to 5 carbon atoms, phenyl, or phenoxy; and wherein platinum complexes of 2-deoxystreptamine in which $X_2$ is the residue of a dicarboxylic acid derivative are excluded.

The present platinum complexes are highly soluble in water, have inhibitory action, for example, against the growth of L 1210 (mouse leukemia cells), S-180 and Colon-38, also show inhibitory action against the growth of cisplatin-resistance cells, and hence can be used as anti-tumor agents having surprisingly superior characteristics.

The platinum sulfate complexes of the present invention may be prepared by mixing a cis-dichlorodiaminocyclohexanolplatinum(II), or a cis-dichloro-1,3-diaminocyclohexaneplatinum(II), with silver sulfate, filtering off the silver chloride thus formed, concentrating the filtrate, and adding ethanol to the concentrate.

Salts of organic acids may be prepared by mixing a cis-dichloro-diaminocyclohexanolplatinum(II), or a cis-dichloro-1,3-diaminocyclohexaneplatinum(II), with silver nitrate, filtering off the silver chloride thus formed, adding an organic acid, such as oxalic, glycolic and cyclobutane-1,1-dicarboxylic acids, to the filtrate, neutralizing the mixture with caustic soda, allowing the resulting solution to stand, collecting the precipitate thus formed, and purifying the same by known techniques, such as recrystallization and treatment with activated charcoal.

The starting material cis-dichlorodiaminocyclohexanolplatinum(II) can be easily obtained by adding an aqueous solution of a diaminocyclohexanol hydrochloride or hydrobromide to an aqueous solution of potassium chloroplatinate, neutralizing the reaction mixture with sodium bicarbonate, allowing the resulting solution to stand in a refrigerator, collecting the crystals thus formed by filtration, and then washing the same. Diaminocyclohexanols can be synthesized according to the method reported by some of the present inventors. See Bull. Chem. Soc. Jpn., 37, 733 (1964); 38, 758 (1965); 38, 2026 (1965); 39, 170 (1966); 40, 1295 (1967) or by the method reported in J. Amer. Chem. Soc., 80, 752 (1958).

Another starting material, cis-dichloro-1,3-diaminocyclohexaneplatinum(II), can also be prepared by the reaction of 1,3-diaminocyclohexane and potassium chloroplatinate in the same manner as described above.

The platinum complexes thus obtained may be used as an anti-tumor agent, for example, in the form of a suspension.

The suitable unit dose of active ingredient is in the range of about 0.01 to 2000 mg, i.e., a total of 0.02 to 500 mg a day. The amount actually used may be varied within the above range depending on the severity of disease, body weight of patient and other factors generally accepted by those skilled in the art.

The present compounds may be mixed with physiologically acceptable additives, such as a vehicle, carrier, excipient, binder, preservative, stabilizer and perfume, and fabricated into commonly used dosage forms so that each unit dose will contain the active ingredient in the amount of 0.02 to 500 mg.

Parenteral injections can be prepared by dissolving or suspending the active ingredient in sterile water together with a vegetable oil, such as sesame oil, coconut oil, peanut oil and cottonseed oil, or a synthetic oily vehicle, such as ethyl oleate, and, as required, a buffering agent, preservative, antioxidant or other additives.

The present invention will now be further illustrated by reference to the following examples which are solely for the purpose of illustration and are not intended to limit the present invention.

EXAMPLE 1

Cis-oxalato-(1/2,3)-2,3-diamino-1-cyclohexanol-platinum(II) (Compound No. 1)

A mixture of 792 mg cis-dichloro(1/2,3)-2,3-diamino-1-cyclohexanolplatinum(II), 680 mg silver nitrate and 12 ml water was heated with stirring in a dark place at 60° to 65° C. for three hours. The reaction mixture was filtered, the precipitate on the filter was washed with water, and the washings were added to the filtrate. To the combined solution, was added 12 ml of 0.2M aqueous solution of disodium oxalate (pH 6), the mixture was stirred overnight at room temperature and then concentrated to about 10 ml, and the concentrate was allowed to stand in a refrigerator. The white precipitate which separated out was collected by filtration, washed with ethanol and dried, giving 684 mg (yield: 79%) of the product.

IR (KBr): 3427, 3323, 3197, 3125, 1696, 1679, 1579, 1414, 1274, 1072, 813, 657, 560 (cm$^{-1}$).

$^1$H-NMR (DMSO-d$_6$)

δ: 1.1–1.9 (m, 7H), 2.3 (m, 1H), 2.8 (m, 1H), 3.7 (m, 1H), 5.0–5.5 (m, 2H, —NH$_2$), 5.9–6.1 (m, 2H, —NH$_2$).

Melting point: 247°–248° C. (dec.

Elemental analysis C$_8$H$_{14}$N$_2$O$_5$Pt.1H$_2$O (M.W.:431.30)

Calc. (%) C: 22.28 H: 3.94 N: 6.50.

Found (%) C: 22.24 H: 3.99 N: 6.63.

Solubility: 3.1 mg/ml (in physiological saline).

EXAMPLE 2

Cis-sulfato-(1/2,3)-2,3-diamino-1-cyclohexanol-platinum(II) (Compound No. 2)

A mixture of 792 mg cis-dichloro-(1/2,3)-2,3-diamino-1-cyclohexanolplatinum(II), 624 mg silver sulfate and 30 ml water was stirred in a dark place at room temperature for three hours. The reaction mixture was filtered, the precipitate on the filter was washed with water, the washings were added to the filtrate, and the combined solution was concentrated. The residue was dissolved in 2 ml water, 10 ml ethanol was added to the solution, and the mixture was kept cooled in ice for three hours. The faint-yellow precipitate which separated out was collected by filtration, washed with ethanol and dried, giving 554 mg (yield: 66%) of the product.

IR (KBr): 3216, 1594, 1455, 1122, 1030, 942, 666, 617 (cm$^{-1}$).

$^1$H-NMR (DMSO-d$_6$).

δ: 1.1–1.9 (m, 7H), 3.15 (m, 1H), 3.7 (m, 1H), 5.3 (m, 1H), 5.0–5.5 (m, 2H, —NH$_2$), 6.1–6.6 (m, 2H, —NH$_2$).

Melting point: 178°–179° C. (dec.).

Solubility: >20.0 mg/ml (in physiological saline).

EXAMPLE 3

Cis-glycolato-(1/2,3)-2,3-diamino-1-cyclohexanol-platinum(II) (Compound No. 3)

A mixture of 792 mg cis-dichloro-(1/2,3)-2,3-diamino-1-cyclohexanolplatinum(II), 680 mg silver nitrate and 12 ml water was heated in a dark place with stirring at 60° to 65° C. for three hours. The reaction mixture was filtered, the precipitate on the filter was washed with water, and the washings were added to the filtrate. To the combined solution, was added 157 mg glycolic acid dissolved in 2 ml water and neutralized with 30% caustic soda solution to pH 7, and the mixture was stirred overnight at room temperature. The reaction mixture was concentrated, the residue was dissolved in 2 ml water, 10 ml ethanol was added to the solution, and the mixture was kept cooled in ice for three hours. The faint-yellow precipitate which separated out was collected by filtration, washed with ethanol and dried, giving 270 mg (yield: 31%) of the product.

IR (KBr): 3513, 3464, 3198, 3111, 1621, 1584, 1402, 1308, 1086, 1077, 989, 861 (cm$^{-1}$).

$^1$H-NMR (DMSO-d$_6$)

δ: 1.1–1.9 (m, 7H), 2.3 (m, 1H), 2.8 (m, 1H), 3.7 (m, 1H), 4.2 (s, 2H).

Melting point: 206°–208° C. (dec.)

Elemental analysis C$_8$H$_{16}$N$_2$O$_4$Pt.2.25H$_2$O (M.W. 439.84) Calc. (%) C: 21.85 H: 4.70 N: 6.37. Found (%) C: 21.27 H: 4.10 N: 6.51.

Solubility: 4.4 mg/ml (in physiological saline).

EXAMPLE 4

Cis-oxalato-1,3-diaminocyclohexaneplatinum(II) (Compound No. 4)

A mixture of 2.29 g 1,3-diaminocyclohexane, 8.3 g K$_2$PtCl$_4$ and 120 ml water was stirred overnight at room temperature, and the brown precipitate which separated out was collected on a glass filter and washed with cold water. The crude crystals thus obtained (5.37 g) were dissolved in 630 ml 1N-HCl, the solution was heated with stirring at 70° to 80° C. for three hours, and the reaction mixture was cooled to room temperature. The faint-yellow precipitate which separated out was collected by filtration, washed with water and acetone in that order, and dried under reduced pressure, giving 2.41 g (yield: 32%) of cis-dichloro-1,3-diaminocyclohexaneplatinum(II).

IR (KBr): 3232, 1588, 1450, 1391, 1272, 1213, 1179, 997 (cm$^{-1}$).

Melting point: 238°–240° C. (dec.).

Elemental analysis: C$_6$H$_{14}$N$_2$Cl$_2$Pt (M.W.: 380.18). Calc. (%) C: 18.96 H: 3.71 N: 7.37. Found (%) C: 18.48 H: 3.65 N: 7.24.

This compound (760 mg) was mixed with 680 mg silver nitrate and 12 ml water, and the mixture was heated in a dark place with stirring at 60° to 65° C. for three hours. The reaction mixture was filtered, the precipitate on the filter was washed with water, and the washings were added to the filtrate. To the combined solution, was added 12 ml of 0.2M aqueous solution of disodium oxalate (prepared by neutralizing oxalic acid dihydrate with 30% caustic soda solution to pH 6), and the mixture was stirred overnight at room temperature. The reaction mixture was treated with activated charcoal and concentrated, the residue was dissolved in 2 ml water, 10 ml ethanol was added to the solution, and the mixture was kept cooled in ice for about three hours. The white precipitate which separated out was collected by filtration, washed with ethanol and dried, giving 334 mg (yield: 42%) of the product.

IR (KBr): 3233, 1694, 1670, 1455, 1380, 1296, 815, 790, 0.557 (cm$^{-1}$).

$^1$H-NMR (D$_2$O).

δ: 1.6–2.1 (m, 7H), 2.6–3.0 (m, 2H), 4.3–4.5 (m, 1H).

Melting point: 235°–237° C. (dec.).

Elemental analysis C$_8$H$_{14}$N$_2$O$_4$Pt (M.W.: 397.29). Calc. (%) C: 24.19 H: 3.50 N: 7.05. Found (%) C: 24.18 H: 3.36 N: 6.90.

Solubility: 8.0 mg/ml (in physiological saline).

EXAMPLE 5

Cis-sulfato-1,3-diaminocyclohexaneplatinum(II) (Compound No. 5)

A mixture of 380 mg cis-dichloro-1,3-diaminocyclohexaneplatinum(II) (prepared in the same manner as in Example 4), 312 mg silver sulfate and 15 ml water was stirred in a dark place at room temperature for about three hours. The reaction mixture was filtered, the precipitate on the filter was washed with water, the washings were added to the filtrate, and the combined solution was concentrated. The residue was dissolved in 1 ml water, 5 ml ethanol was added to the solution, and the mixture was kept cool in ice for about three hours. The precipitate which separated out was collected by filtration, washed with ethanol and dried, giving 270 mg (yield: 61%) of the product as white crystals.

IR (KBr): 3201, 1586, 1451, 1138, 997, 640, 622 (cm$^{-1}$).

Melting point: 239°–241° C. (dec.).

Elemental analysis $C_6H_{14}N_2O_4SPt.2H_2O$ (M.W.: 441.36).

Calc. (%) C: 16.33 H: 4.11 N: 6.35. Found (%) C: 16.17 H: 4.11 N: 6.21.

EXAMPLE 6

Cis-cyclobutane-1,1-dicarboxylato-1,3-diaminocyclohexaneplatinum(II) (Compound No. 6)

A mixture of 863 mg cis-dichloro-1,3-diaminocyclohexaneplatinum(II) (prepared in the same manner as in Example 4), 771 mg silver nitrate and 20 ml water was heated with stirring in a dark place at 60° to 65° C. for three hours. The reaction mixture was filtered, the precipitate on the filter was washed with water, the washings were added to the filtrate. To the combined solution, was added 327 mg cyclobutane-1,1-dicarboxylic acid dissolved in 2 ml water and neutralized with 30% caustic soda solution to pH 7, and the solution was heated with stirring at 60°–65° C. for three hours. The reaction mixture was cooled in ice, and the precipitate which separated out was collected by filtration, washed with water and dried. The brown crude crystals (322 mg) thus obtained were dissolved in 35 ml methanol by heating, the solution was treated with activated charcoal, concentrated to remove the methanol and cooled, and the crystals were separated out were collected by filtration, washed with methanol and dried, giving 61 mg (yield: 6%) of pure product as white crystal.

IR (KBr): 3448, 3198, 2930, 2859, 1615, 1459, 1364, 1280, 906, 761 (cm$^{-1}$).

Elemental analysis $C_{12}H_{20}N_2O_4Pt$ (M.W.: 451.38). Calc. (%) C: 31.93 H: 4.46 N: 6.21. Found (%) C: 31.48 H: 4.05 N: 6.15.

EXAMPLE 7

Cis-sulfato-2-deoxystreptamineplatinum(II) (Compound No. 7)

A mixture of 428 mg cis-dichloro-2-deoxystreptamineplatinum(II), 312 mg silver sulfate and 10 ml water was stirred in a dark place at room temperature for three hours. The reaction mixture was filtered, the precipitate on the filter was washed with water, the washings were added to the filtrate, and the combined solution was concentrated. The residue was dissolved in 2 ml water, 10 ml ethanol was added to the solution, and the mixture was kept cooled in ice for about three hours. The faint-yellow crystals which separated out were collected by filtration, washed with ethanol and dried, giving 110 mg (yield: 22%) of pure product.

IR (KBr): 3230, 1626, 1533, 1406, 1110, 1035, 617 (cm$^{-1}$).

Elemental analysis $C_6H_{14}N_2O_7SPt.2H_2O$ (M.W.: 489.36) Calc. (%) C: 14.73 H: 3.71 N: 5.72. Found (%) C: 15.11 H: 3.76 N: 5.65.

Shown below are the structures of Compounds No. 1 to 7 prepared above.

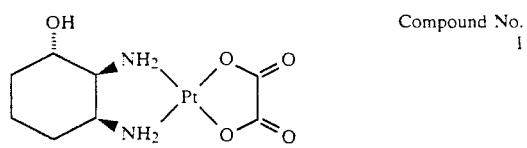

Compound No. 1

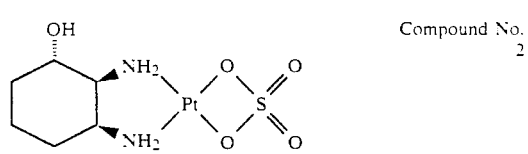

Compound No. 2

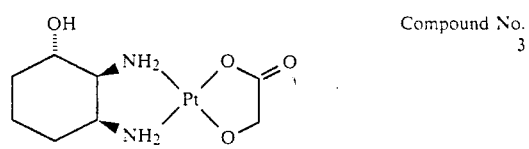

Compound No. 3

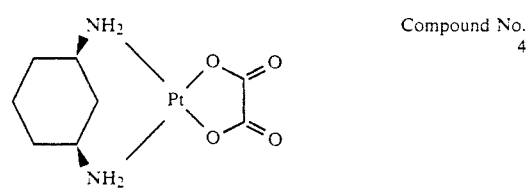

Compound No. 4

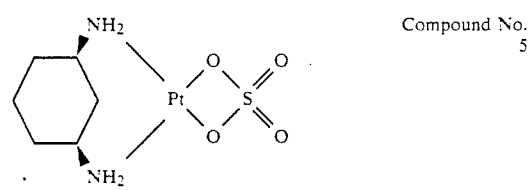

Compound No. 5

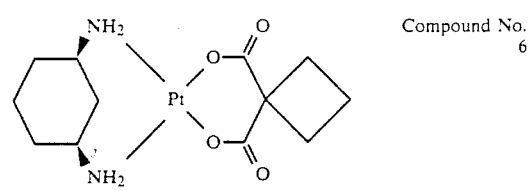

Compound No. 6

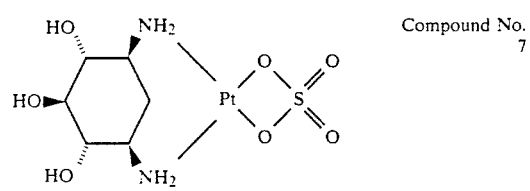

Compound No. 7

EXAMPLE 8

(+)-Cis-sulfato-(1/2,3)-2,3-diaminocyclohexanolplatinum(II) (Compound No. 8)

(−)-Cis-sulfato-(1/2,3)-2,3-diaminocyclohexanoplatinum(II) (Compound No. 9)

5g (±)-(1/2,3)-2,3-diaminocyclohexanol dihydrochloride was suspended in 3 ml dichloromethane, and thereto 7.48 g triethylamine, 19.8 g Naproxen and 0.3 g dimethylaminopyridine were added and then the mixture was stirred to be homogeneous. After adding 20 g water-soluble carbodiimide (WSC), the mixture was stirred while cooling in ice for 10 minutes, then at room temperature for 42 hours. The mixture was concentrated under reduced pressure and the residue was diluted with ethyl acetate, washed with 10% citric acid, 7% NaHCO$_3$, water and brine, and dried over Na$_2$SO$_4$. The solvent was evaporated and the residue was purified by column chromatography (Merck Lobar column, Si60,C, ethyl acetate: hexane 2:1–3:1), giving 8.79 g of less-polar-isomer (yield: 47%) and 8.39 g of more-polar-isomer (yield: 44%) as faint-yellow foam. 9.1 g of less-polar-isomer was added to 20 ml ethanol, 30 ml water and 60 ml conc.HCl, and the mixture was heated at reflux temperature for 36 hours. Ethanol was evaporated, the aqueous solution was washed with ether, and then was concentrated to give 2.42 g of red-brown solids. The solids were dissolved in 30 ml methanol while heating, then cooled, and 20 ml ether were added with stirring. The obtained gel was filtrated and the precipitate on the filter was washed with methanol:ether (1:1) and ether, and then dried under vacuum. (−)-(1/2,3)-2,3-Diaminocyclohexanol dihydrochloride 1.704 g (yield: 72%) was obtained as a white solid. By the same method as above, from 7.96 g of polar-isomer, (+)-(1/2,3)-2,3-diaminocyclohexanol dihydrochloride 1.6 g (yield: 76%) was obtained as a white solid. (−)-(1/2,3)-2,3-diaminocyclohexanol dihydrochloride:

$$[\alpha]_D^{22} = -39.0 \ (c=1.0, \ 1 \ N \ HCl)$$

(+)-(1/2,3)-2,3-diaminocyclohexanol dihydrochloride:

$$[\alpha]_D^{22} = +40.2 \ (c=1.0, \ 1 \ N \ HCl)$$

1.88 g (−)-(1/2,3)-2,3-Diaminocyclohexanol dihydrochloride and 3.84 g K$_2$PtCl$_4$ were dissolved in 28.2 ml water, 1.56 g NaHCO$_3$ was added thereto, and after stirring at room temperature for 30 minutes the mixture was kept in the refrigerator for 4 days. The precipitated crystals were collected by filtration, washed with cooled-water, ethanol, ethyl, acetate and ether, dried under vacuum to give (+)-cis-dichloro-(1/2,3)-2,3-diaminocyclohexanolplatinum(II) 2.97 g (yield: 81%). 2.5 g of this dichloro-Pt(II)-complex was suspended in 7.5 ml water, 1.97 g Ag$_2$SO$_4$ was added thereto, stirred in a dark place at room temperature for 3 hours. The solution was filtrated, and the filtrate was concentrated under reduced pressure. The residue was dissolved in 5 ml water and added slowly to 40 ml ethanol, and the solution was kept in the refrigerator for 1 hour. The precipitated crystals were collected by filtration, and faint-yellow crystals were obtained. These crystals were washed with ethanol, dried under vacuum to give the product of Compound No. 8 (2.37 g) (yield: 82%).

IR (KBr): 3217, 2939, 1596, 1455, 1116, 1029, 941, 666, 612 (cm$^{-1}$)

Melting point: 178°–179° C. (dec.)

$^1$H-NMR (D$_2$O-TSP)

δ: 1.2–2.2 (m, 4H), 2.4–2.8 (m, 1H), 3.2–3.4 (m, 1H); 4.0–4.2 (m, 1H), 5.0–6.5 (M, 4H).

$^{13}$C-NMR (D$_2$O-TSP) ppm: 20.3, 27.8, 33.7 (CH$_2$); 62.8, 67.2, 69.7 (CH).

$[\alpha]_D^{22} = +11.6 \ (c=1.0, \ H_2O)$.

By the same method as above, 0.62 g of (−)-cis-dichloro-(1/2,3)-2,3-diaminocyclohexanolplatinum(II) (yield: 85%) was obtained from 1.83 g (+)-(1/2,3)-2,3-diaminocyclohexanol dihydrochloride and from 2.5 g of this Pt complex, the product of Compound No. 9 (2.60 g) (yield: 90%) was obtained.

IR (KBr): 3215, 2941, 1595, 1455, 1121, 1029, 942, 668, 615 (cm$^{-1}$).

Melting point: 177°–179° C. (dec.).

$^1$H-NMR (D$_2$O-TSP) δ: 1.2–2.1 (m, 4H), 2.4–2.8 (m, 1H), 3.2–3.4 (m, 1H) 3.8–4.1 (m, 1H), 5.0–6.2 (m, 4H).

$^{13}$C-NMR (D$_2$O-TSP) ppm: 20.4, 27.9, 33.8 (CH$_2$). 62.3, 67.2, 69.7 (CH).

$[\alpha]_D^{22} = -22.0 \ (c=1.0, \ H_2O)$.

EXAMPLE 9

Anti-tumor activity testing 1

(1) Test animals

Female ICR/CRJ mice of 5-week age were used as test animals (five head for each group).

(2) Test method

Sarcoma-180 cells (1×10$^6$) were intraperitoneally transplanted to each of the test animals, each of the Pt(II) complexes listed in Table 1 was then injected intraperitoneally on the next day, and the life-prolonging rate was measured for each test group. Physiologically saline was used as the solvent of injections.

The results are summarized in Table 1, which show the excellent anti-tumor activity of the present platinum complexes.

TABLE 1

| Compound No. | Life-prolonging Rate (%) Dose (mg/Kg × 1) | | | |
|---|---|---|---|---|
| | 4.0 | 8.0 | 16.0 | 32.0 |
| 1 | 189 | 218 | 266 | |
| 2 | 295 | 532 | 534 | |
| 3 | 212 | 182 | 252 | |
| 4 | 248 | 258 | 364 | |
| 5 | 202 | 187 | 236 | |
| 6 | | | 126 | 106 |
| 7 | | 126 | 120 | 241 |

EXAMPLE 10

Anti-tumor activity testing 2

(1) Test animals

Female BDF$_1$ mice of 5-week age were used as test animals (five head for each group).

(2) Test method

L1210 cells (1×10$^5$) were intraperitoneally transplanted to each of the test animals, each of the Pt(II) complexes listed in Table 2 was then injected intraperitoneally one day, five days and nine days after transplantation (a total of three times), and the life-prolonging rate was measured for each test group. Physiologically saline was used as the solvent of injections.

The results are summarized in Table 2, which show the excellent anti-tumor activity of the present platinum complexes.

TABLE 2

| Compound No. | Life-prolonging Rate (%) Dose (μmol/Kg × 3) | | | |
|---|---|---|---|---|
| | 7.5 | 15.0 | 30.0 | 60.0 |
| 1 | 115 | 115 | 132 | |
| 2 | 136 | 134 | 151 | |
| 3 | 116 | 122 | 147 | |
| 4 | 127 | 222 | 245 | |
| 5 | 121 | 189 | 155 | |
| 6 | | | 98 | 104 |

TABLE 2-continued

| Compound No. | Life-prolonging Rate (%) Dose (μmol/Kg × 3) | | | |
|---|---|---|---|---|
| | 7.5 | 15.0 | 30.0 | 60.0 |
| 7 | | 102 | 109 | 119 |

EXAMPLE 11

Anti-Tumor Activity Testing 3

(1) Test Animals female BDF mice of 5-week age were used as test animals (five head for each group).

(2) Test method

Colon 38 cells (40 mg) were subcutaneously transplanted to each of the test animals at the haunch, each of the Pt(II) complexes listed in Table 3 was then injected intraperitoneally 1 day, 8 days and 15 days after transplantation (a total of three times), and the tumor-growth inhibition rate was measured for each test group 21 days after transplantation.

The results are summarized in Table 3, which show the excellent anti-tumor activity of the present platinum complexes.

TABLE 3

| Compound No. | Tumor-growth Inhibition Rate (%) Dose (μmol/Kg × 3) | | |
|---|---|---|---|
| | 20.0 | 30.0 | 45.0 |
| 1 | 24 | 16 | 45 |
| 2 | 47 | 78 | 97 |
| 3 | 70 | 72 | 96 |
| 4 | 54 | 77 | 88 |
| 5 | 36 | 56 | 56 |

EXAMPLE 12

Test inhibitory activity against the growth of cis-platin-resistant cells

L1210 cells and cisplatin-resistant L1210 cells under subcultivation were incubated in RPMI1640 medium containing 10% fetal bovine serum at 37° C. for 46 hours in an atmosphere containing 5% carbon dioxide. [$^3$H]-thymidine was added to the grown cells, and incubation was continued for an additional two hours. The growth inhibition rate of a drug was calculated from the amounts of [$^3$H]-thymidine taken into the cells in the presence and absence of that drug, and the 50% growth inhibition concentration (IC$_{50}$) was determined from the graph of inhibition rate plotted against drug concentration. The degree of drug resistance was calculated from the ratio of IC$_{50}$ for cisplatin-resistant L1210 cells to that for L1210 cells.

The results are summarized in Table 4, which indicate that the platinum complexes of this invention show practically no cross reference with cisplatin.

TABLE 4

| Compound No. | IC$_{50}$(L1210 cells) (μM) | IC$_{50}$(resistant cells) (μM) | Degree of Resistance |
|---|---|---|---|
| Cisplatin | 1.0 | 10.5 | 10.5 |
| 1 | 3.5 | 6.6 | 1.9 |
| 2 | 1.7 | 3.2 | 1.9 |
| 3 | 1.3 | 2.5 | 1.9 |
| 4 | 2.4 | 5.0 | 2.1 |
| 5 | 3.1 | 7.9 | 2.5 |

EXAMPLE 13

Anti-tumor activity testing 4

(1) Test animals

Female BDF mice of 5-week age were used as test animals (eight head for each group).

(2) Test method

Colon 38 cells (40 mg) were subcutaneously transplanted to each of the test animals at the haunch, each of the Pt(II) complexes listed in Table 5 was then injected intravenously 1 day, 5 days, 9 days, 12 days, days and 20 days after transplantation (a total of 6 times), and the tumor-growth inhibition rate was measured for each test group 21 days after transplantation.

The results are summarized in Table 5.

TABLE 5

| Compound No. | Tumor-growth Inhibition Rate (%) Dose (mg/kg × 6) | | | | |
|---|---|---|---|---|---|
| | 1 | 2 | 4 | 8 | 16 |
| 2 | — | 22 | 41 | 90 | toxic |
| 8 | — | 34 | 35 | 61 | 91 |
| 9 | — | 40 | 88 | 88 | toxic |
| Cisplatin | 19 | 58 | 84 | toxic | — |

Having now fully described the present invention, it will be apparent to one of ordinary skill in the art that a variety of modifications may be made to the above description while remaining within the spirit and scope of the present invention.

What is claimed as new and desired to be secured by Letters Patent of the United States is:

1. The platinum complexes of cis-diaminocyclohexanol having the following formula:

wherein $X_2$ is a radical selected from the group consisting of $R^9$ is hydrogen, hydroxyl, lower alkyl or phenyl; and $R^{10}$ is hydrogen, hydroxyl, amino, dimethylamino, N-acetylamino, piperidino, pyrrolidino, lower alkyl, lower alkoxy, phenyl or phenoxy.

2. The platinum complex of claim 1 which is

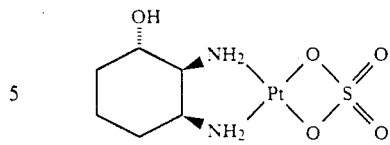
4. The platinum complex of claim 1 which is
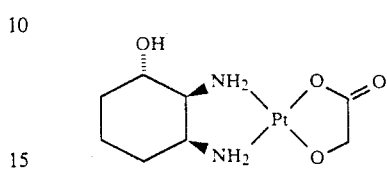
5. An anti-tumor composition, comprising an effective amount of one or more of the compounds of claim 1, and a pharmaceutically acceptable excipient.
6. The anti-tumor composition of claim 5, wherein the effective amount is about 0.01 to 2,000 mg.
* * * * *
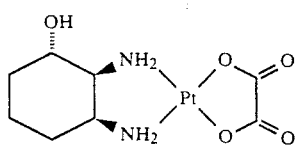
3. The platinum complex of claim 1 which is